(12) United States Patent
Wong et al.

(10) Patent No.: US 6,589,235 B2
(45) Date of Patent: Jul. 8, 2003

(54) METHOD AND APPARATUS FOR CARTILAGE RESHAPING BY RADIOFREQUENCY HEATING

(75) Inventors: Brian J. F. Wong, Irvine, CA (US); Thomas E. Milner, Austin, TX (US); Emil N. Sobol, Moscow (RU); Michael W. Keefe, Orange, CA (US)

(73) Assignees: The Regents of the University of California, Oakland, CA (US); The Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/770,799

(22) Filed: Jan. 19, 2001

(65) Prior Publication Data

US 2002/0016588 A1 Feb. 7, 2002

Related U.S. Application Data

(60) Provisional application No. 60/177,543, filed on Jan. 21, 2000.

(51) Int. Cl.$^7$ .......................... A61B 18/04; A61B 18/18
(52) U.S. Cl. .............................. 606/32; 606/34; 606/41
(58) Field of Search ............................. 606/32, 34, 35, 606/41, 42; 607/96, 101, 102, 115, 148

(56) References Cited

U.S. PATENT DOCUMENTS

| 4,326,529 | A |   | 4/1982  | Doss et al. |
|-----------|---|---|---------|-------------|
| 4,381,007 | A |   | 4/1983  | Doss |
| 5,458,596 | A | * | 10/1995 | Lax et al. ................... 606/31 |
| 5,569,242 | A |   | 10/1996 | Lax et al. |
| 5,670,538 | A | * | 9/1997  | Franchimont, deceased et al. ........... 514/456 |
| 5,935,123 | A | * | 8/1999  | Edwards et al. .............. 606/41 |
| 6,053,909 | A | * | 4/2000  | Shadduck ................... 606/16 |
| 6,068,628 | A | * | 5/2000  | Fanton et al. ................ 606/28 |
| 6,105,581 | A | * | 8/2000  | Eggers et al. ............... 128/898 |
| 6,146,385 | A | * | 11/2000 | Torrie et al. ................. 606/80 |
| 6,159,194 | A |   | 12/2000 | Eggers |
| 6,235,020 | B1 | * | 5/2001 | Cheng et al. ............... 604/114 |
| 6,311,090 | B1 | * | 10/2001 | Knowlton ................... 606/41 |
| 6,322,584 | B2 | * | 11/2001 | Ingle et al. .................. 606/27 |
| 6,350,276 | B1 | * | 2/2002 | Knowlton ................... 607/101 |
| 6,358,273 | B1 | * | 3/2002 | Strul et al. .................. 607/101 |

FOREIGN PATENT DOCUMENTS

| RU | 2114569    | 7/1998 |
| RU | WO 01/22863 | 4/2001 |

OTHER PUBLICATIONS

A. Sviridov, E. Sobol, N. Jone, J. Lowe, "The Effect of Holmium Laser Radiation on Stress, Temperature and Structure of Cartilage", Laser Med Sci, (U.K.), 1998, vol. 13, pp. 73–77.

B. Wong, T. Milner, B. Anvari, A. Sviridov, A. Omel'chenko, V. Bagratashvili, E. Sobol and J. Nelson, "Measurement of Radiometric Surface Temperature and Integrated backscattered Light Intensity During Feedback–Controlled Laser–assisted Cartilage Reshaping", Lasers in Medical Science, (U.S.A.), Feb. 20, 1998, pp. 1–7.

(List continued on next page.)

Primary Examiner—Linda C. M. Dvorak
Assistant Examiner—Kenneth G Schopfer
(74) Attorney, Agent, or Firm—Daniel L. Dawes; Myers Dawes Andras & Sherman LLP

(57) ABSTRACT

A method and apparatus for reshaping cartilage using radiofrequency heating. The cartilage temperature is raised sufficiently for stress relaxation to occur in the cartilage, but low enough so that significant denaturation of the cartilage does not occur. The RF electrodes may be designed to also function as molds, preses, clamps, or mandrills to deform the cartilage tissue. Changes in various properties of the cartilage associated with stress relaxation in the cartilage may be measured in order to provide the control signal to provide effective reshaping without denaturation.

39 Claims, 4 Drawing Sheets

OTHER PUBLICATIONS

E. Sobol, M. Kitai, N. Jones, A. Sviridov, T. Milner, and B. Wong, "Theoretical Modeling of heating and structure alterations in cartilage under laser radiation with regard to water evaporation and diffusion dominance", SPIE vol. 3254, (U.S.A.), 1998, pp. 54–63.

N. Bagratashvili, A. Sviridov, E. Sobol, and M. Kitai, "Optical properties of nasal septum cartilage", SPIE vol. 3254, (U.S.A), 1998, pp. 398–406.

B.J.F. Wong, T.E. Milner, H.H. Kim, J.S. Nelson and E.N. Sobol, "Stress Relaxation of Porcine Septal Cartilage During Nd:YAG(1=1.32 mm) Laser Irradiation: Mechanical, Optical and Thermal Responses", Journal of Biomedical Optics, (U.S.A.), vol. 3, No. 4, Oct. 1998, pp. 409–414.

Chew, C; Wong, B J.; Milner, T E.; Kim, H K.; Gomez, A; Nelson, S; Sobol, E N. Feedback Controlled Cartilage Reshaping with Nd:YAG Laser: Effects of pH Variation, Proc. SPIE, 1998, vol. 3245, (U.S.A.), pp. 206–216.

E. Sobol, A. Sviridov, M. Kitai, J. Gilligan, N. Tolk, G. Edwards, "Effect of wavelength on threshold and kinetics of tissue denaturation under laser radiation", SPIE vol. 3601, (U.S.A.), 1999, pp. 122–129.

E. Sobol, M. Kitai, N. Jones, A. Svridov, T. Milner, and B. Wong, "Heating and Structural Alterations in Cartilage under Laser Radiation", IEEE Journal, (U.S.A.), vol. 35, No. 4, Apr. 1999, pp. 532–539.

S. Madsen, E. Chu and B. Wong, "The Optical Properties of Porcine Nasal Cartilage", IEEE Journal, (U.S.A.), vol. 5, No. 4, Jul./Aug. 1999, pp. 1127–1133.

B.J.F. Wong, T.E. Milner, H.K. Kim, S.A. Telenkov, C.F. Chew, E.N. Sobol and J.S. Nelson, "Characterization of Temperature–Dependent Biophysical Properties During Laser Mediated Cartilage Reshaping", IEEE Journal, (U.S.A.), vol. 5, No. 4, Jul./Aug. 1999, pp. 1095–1102.

B.J.F. Wong, T.E. Milner, A. Harrington, J. Ro, X. Dao, E.N. Sobol, and J.S. Nelson, "Feedback–Controlled Laser–Mediated Cartilage Reshaping", Archives of Facial Plastic Surgery, (U.S.A.), vol. 1, Oct.–Dec. 1999, pp. 282–287.

A.Sviridov, E.Sobol, V.Bagratashvili, A.Omelchenko, Yu.Ovchinnikov, A.Shekhter, V.Svistushkin, A.Shinaev,G. Nikiforova, N.Jones, "In vivo study and histological examination of laser reshaping of cartilage", SPIE, (U.S.A.), Jan. 1999, vol. 3590, pp. 222–228.

E. Sobol, A. Omel'chenko, M. Mertig, W. Pompe, Scanning Force Microscopy of the Fine Structure of Cartilage Irradiated with a CO2 Laser, Lasers in Medical Science, vol. 15, 15–23 (2000), (U.S.A.).

K. K. H. Chao, B. J. F. Wong, H. K. Kim, T. E. Milner, C.–H. Sung, E. N. Sobol, J. S. Nelson, "Viability of Porcine Nasal Septal Cartilage Grafts Following Nd:YAG (?=1.32–¦m) Laser Radiation", SPIE vol. 3914, 543–552 (2000), (U.S.A.).

E. Sobol, A. Sviridov, A. Omel'chenko, V. Bagratashvili, M. Kitai, S.E. Harding, N. Jones, K. Jumel, M. Mertig, W. Pompe, Y. Ovchinnikov, A. Shekhter and V. Svistushkin, "Laser Reshaping of Cartilage", Biotechnology and Genetic Engineering Reviews, (U.K.), vol. 17., pp. 539–564, Aug. 2000.

E. Sobol, A. Sviridov, V. Bagratashvili, A. Omel'chenko, Y. Ovchinnikov, A. Shekhter, V. Svistushkin, and A. Shinaev, "Laser reshaping of nasal septum cartilage: clinical results for 40 patients", SPIE vol. 3907 (2000), (U.S.A.), pp. 297–302.

Keefe, Wong and Crumley, "Stress Relaxation of Porcine Septal Cartilage during Radio–Frequency Generated Heating", published May 2000, in Lasers in Surgery: Advanced Characterization, Therapeutics, and Systems, Proceedings SPIE vol. 3907, p. 289–296.

Presentation made by Keefe at a meeting of the ENT Society in San Diego, CA, approx. Feb./Mar. 2000. Substantively cumulative to document D1, copy not provided.

Presentation by Keefe made at meeting of the ENT Department at UC Irvine,CA, around Jun. 10, 2000.

Presentation by Keefe made at a meeting of the American Academy of Otolaryngology—Head and Neck Surgery meeting in Washington D.C. in Sep., 2000.

E. Helidonis, E. Sobol, G. Kavvalos, J. Bizakis, P. Christodoulou, G. Velegrakis, J. Segas, and V. Bagratashvili, "Laser Shaping of Composite Cartilage Grafts", Amer. Journal of Otolaryngology, (U.S.A.), vol. 14, No. 6, Nov./Dec. 1993, pp. 410–412.

E. Sobol, V. Bagratashvili, A. Omel'chenko, and A. Sviridov, "Laser Shaping of Cartilage", SPIE vol. 2128, (U.S.A.), 1994, pp. 43–49.

Helidonis, Sobol, Velegrakis, and Bizakis, "Shaping of Nasal Septal Cartilage with the Carbon Dioxide Laser –a Preliminary Report of an Experimental Study", Laser in Medical Science, Harcourt/W.B. Saunders Co., (London, U.K.), 1994, vol. 9, pp. 51–54.

Z. Wang, M. Pankratov, D. Perrault, and S. Shapshay, "Laser–Assisted Cartilage Reshaping: In Vitro and In Vivo Animal Studies", SPIE vol. 2395, (U.S.A.), 1995, pp. 296–302.

E. Sobol, V. Bagratashvil, A. Svirodov, A. Omel'chenko, Y. Ovchinniko, V. Svistushkin, A. Shekhter, N. Jones, S. Howdle, E. Helidonis, "Phenomenon of cartilage shaping using moderate heating and its application in otorhinolaryngology", SPIE 2623, (U.S.A.), 1996, pp. 548–552.

E. Sobol, A. Sviridov, V. Bagratashvili, A. Omel'chenko, Y. Ovchinnikov, A. Shechter, S. Downs, S. Howdie, N. Jones, and J. Lowe, "Stress Relaxation and Cartilage Shaping under Laser Radiation", SPIE 2681, 1996, (U.S.A.), pp. 358–363.

E. Sobol, V. Bagratashvili, A. Sviridov, A. Omel'chenko, M. Kitai, N. Jones, V. Zenger, A. Nasedkin, M. Isaev, V. Karlov, A. Shechter, "Study of cartilage reshaping with holmium laser", SPIE (U.S.A.), vol. 2623, pp. 544–547, 1996.

A. Sviridov, E. Sobol, N. Bagratashvili, V. Bagratashvili, A. Omel'chenko, A. Dmitriev, A. Shechter, Y. Ovchinnikov, V. Svistushkin, G. Nikiforova, N. Jones, J. Lowe, "Dynamics of optical and mechanical properties of cartilage at laser heating", SPIE vol. 2923, (U.S.A.), 1996, pp. 114–117.

V.N. Bagratashvili, E.N. Sobol, A.P. Sviridov, V.K. Popov, A.I. Omel'chenko and S.M. Howdle,"Thermal and Diffusion Processes in Laser–Induced Stress Relaxation and Reshaping of Cartilage", J. Biomechanics, (U.K.), vol. 30, No. 8, 1997, pp. 813–817.

B.J.F. Wong, T.E. Milner, B. Anvari, A. Sviridov, A. Omel'Chenko, V. Bagratashvili, E. Sobol and J.S. Nelson, "Thermo–Optical Response of Cartilage During Feedback Controlled Laser–Assisted Reshaping", SPIE vol. 2970, (U.S.A.), 1997, pp. 380–391.

E. Sobol, A. Sviridov, A. Omel'chenko, V. Bagratashvili, N. Bagratashvili, and V. Popov, "Mechanism of laser–induced stress relaxation in cartilage", SPIE vol. 2975, (U.S.A.), 1997, pp. 310–315.

B.J.F. Wong, T.E. Milner, H.K. Kim, S. Telenkov, C. Chew, T. Kuo, D. Smithies, E.N. Sobol and J.S. Nelson, "Critical Temperature Transitions in Laser Mediated Cartilage Reshaping", SPIE vol. 3245, (U.S.A.), 1998. pp. 161–172.

* cited by examiner

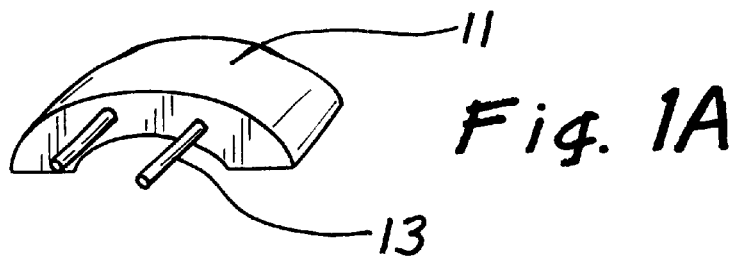
Fig. 1A
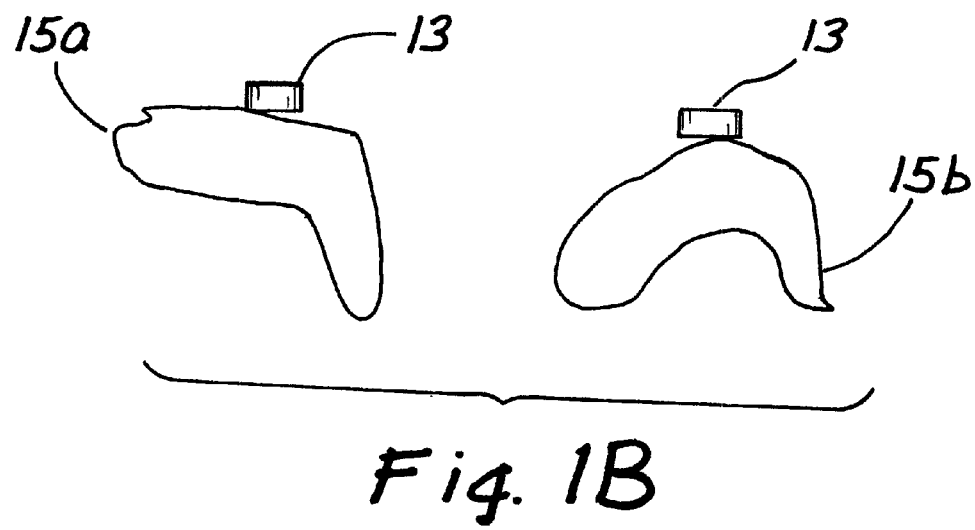
Fig. 1B
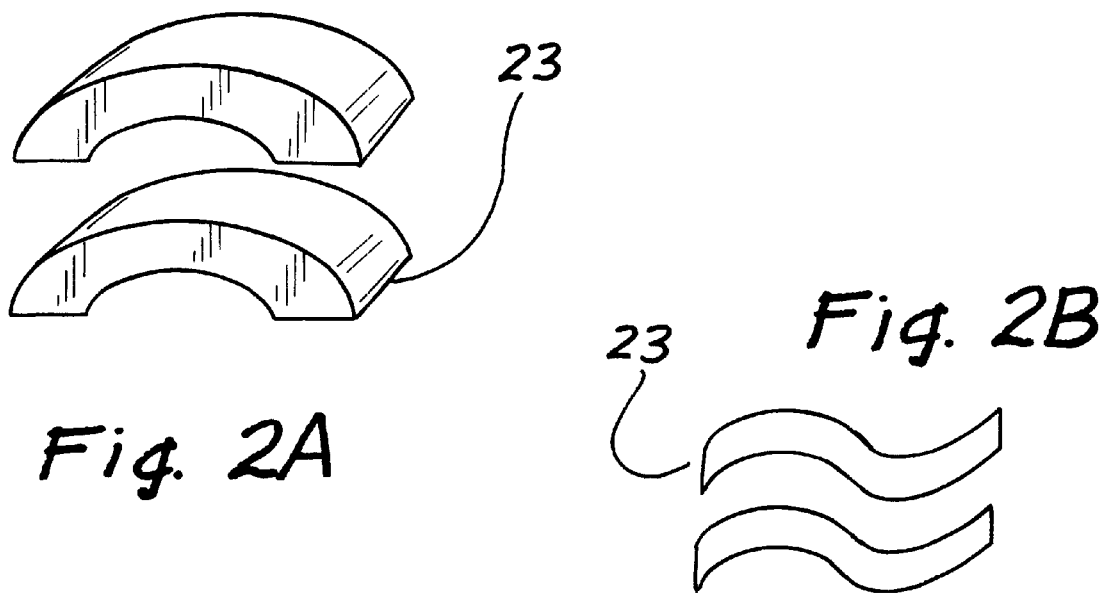
Fig. 2A
Fig. 2B

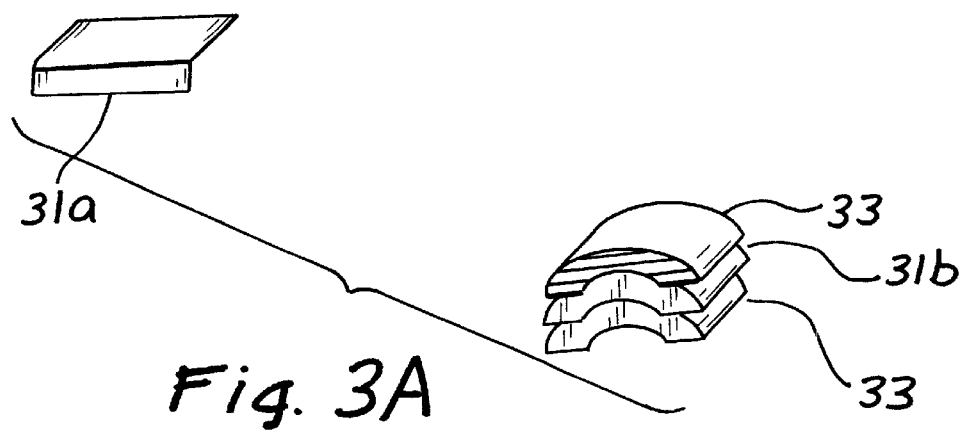
Fig. 3A
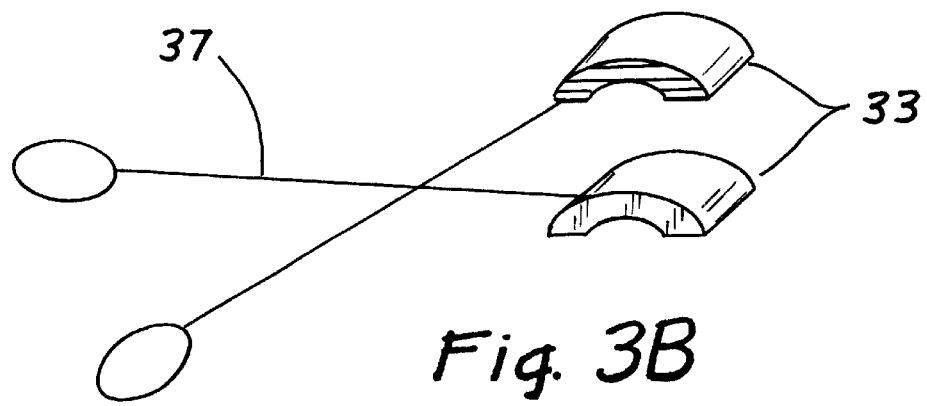
Fig. 3B
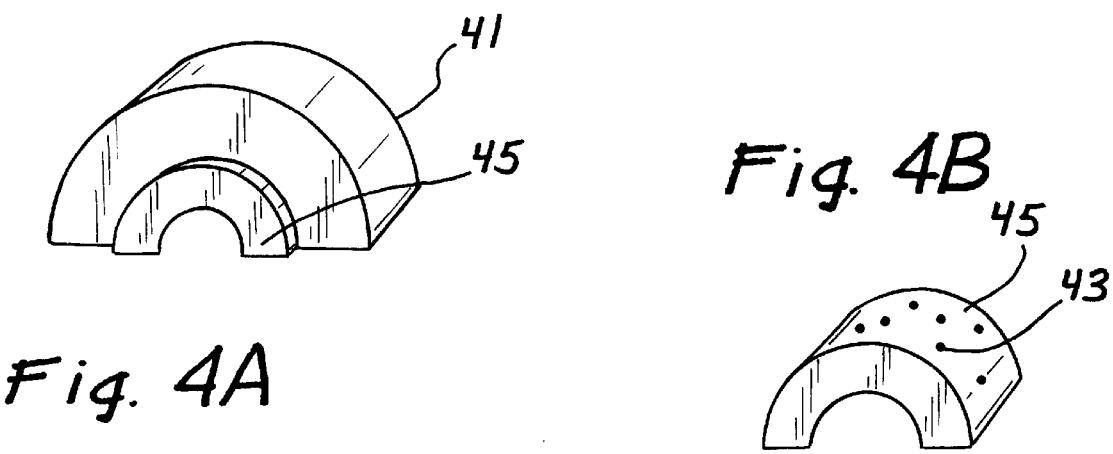
Fig. 4A
Fig. 4B

1

METHOD AND APPARATUS FOR CARTILAGE RESHAPING BY RADIOFREQUENCY HEATING

CROSS-REFERENCE TO RELATED APPLICATIONS

This application claims the benefit of U.S. Provisional Application No. 60/177,543, filed Jan. 21, 2000, entitled "Method and Apparatus for Cartilage Reshaping by Radiofrequency Heating" which is incorporated herein by this reference.

STATEMENT OF GOVERNMENT INTEREST

The United States Government has rights in this invention pursuant to contracts between the University of California, and the Department of Energy (95-3800459); the Office of Naval Research (N00014-94-0874); and the National Institutes of Health (1 K08 DC 00170-01, AR-43419, RR-01192, and HL-59472).

BACKGROUND OF THE INVENTION

1. Field of the Invention

The present invention relates generally to a method and apparatus for reshaping cartilage tissue, by raising the temperature of the cartilage sufficient for relaxation of stress in the cartilage while maintaining the temperature below that at which significant denaturation of the cartilage occurs. The invention particularly relates to a method and apparatus that utilizes radiofrequency heating to induce the stress relaxation.

2. Description of Related Art

Cartilage has long been recognized as an almost ideal autologous grafting material for reconstruction of the anatomy of the upper airway and the head and neck. Conventional reconstructive techniques have involved carving, cutting, suturing and/or morselizing the tissue to alter shape. The limitations of these approaches have been donor site morbidity, depletion of viable donor tissue requiring more radical operative techniques, and the unpredictable outcome of the procedure as a function of the stresses present in the transplanted cartilage or native tissue. The advances made in understanding cartilage at the molecular level have led to an interest in predictably altering its morphology for reconstructive purposes for both grafts and in situ.

Cartilage is a complex macromolecular tissue composed of 80% water, 13% collagen (Type II), and 7% protein-polysaccharide (proteoglycans). The collagen and proteoglycan molecules are synthesized by the chondrocyte, the constitutive cell of cartilage tissue. The collagen forms a rigid framework that encases large meshes of proteoglycan macromolecules containing copious numbers of charged species, chiefly $COO^-$ and $SO_3$ moieties. In the matrix, the proteoglycans are compressed and the surrounding collagen framework resists their expansion. Cations ($Ca^{++}$ and $Na^+$) also permeate the matrix, providing electrical neutrality (charge balance).

Prior to being used in reconstructive or aesthetic procedures, cartilage must often be reshaped because of differences in shape and morphology between the tissue and the constraints of the recipient site. Traditional methods include reshaping by carving, suturing or morselizing. These methods can result in damage to the tissue and decreased viability. In addition, cartilage has a tendency to return to its original shape after mechanical means of reshaping, due to internal stresses present in the cartilage. These points are also valid for operations which alter cartilage shape in situ such as rhinoplasty, tracheoplasty, and otoplasty. The screened Coulomb potential between the negatively charged moieties residing on adjacent proteoglycan molecules resists mechanical deformation of the cartilage. Without intervention, relaxation of stresses normally takes a prohibitively long period of time, which is impractical in the operating room.

Heat can be used to alter the shape of cartilage and create mechanically stable new morphologies. Stress relaxation can result from changes in tissue structure caused by heating of the cartilage, which redistributes tissue water entrapped in the matrix mesh. However, overheating of biological tissue leads to changes in their structure by the processes of denaturation, melting and carbonization connected with chemical bond rupture. There exists a temperature region (60–75 degrees C.) within which molecular bonds are broken resulting in an increase in plasticity of the cartilage, with minimal or no denaturation, melting, carbonization or the boiling of tissue water. Within this region, bound water undergoes the transition to a free state. Upon cooling, this water becomes bound in place, resulting in permanence of shape.

An alternate approach to traditional reconstructive techniques was proposed in 1993 by Helidonis and Sobol, which involved the use of photo-thermal heating to accelerate stress relaxation in deformed cartilage grafts. While numerous studies have focused on the biophysical basis of cartilage shape change during laser irradiation, there are other methods of heating cartilage which include contact heating, ultrasound, and radiofrequency (RF).

Radiofrequency generators are in widespread use in surgery and used commonly to cut or 'fulgurate' tissue or cauterize and coagulate. A newer application is in radiofrequency tissue ablation. Applications of this technique are in the fields of neurosurgery, cardiology, urology, and head and neck surgery, and have been used to treat vertebral disorders such as disc herniation, ablate ectopic cardiac pacemakers, reduce the volume of the prostate, and stiffen the palate to eliminate snoring. These microprocessor controlled devices can maintain tissue temperatures in the 60–90° C. range and heat a controlled volume of tissue surrounding the electrode. U.S. Pat. No. 5,569,242 (Lax et al) discloses the use of RF energy to contract (shrink) collagen tissue.

Unlike tissue ablation or contraction which results in protein denaturation, cartilage reshaping involves thermally mediated stress relaxation preferably without denaturation of the tissue.

SUMMARY OF THE INVENTION

An object of this invention is a method and apparatus for reshaping cartilage via thermally mediated stress relaxation in the cartilage.

A further object of this invention is a method and apparatus for reshaping cartilage which utilizes radiofrequency heating to raise the cartilage temperature to the point where stress relaxation occurs but below that at which significant denaturation of the cartilage occurs.

In the present invention, cartilage is heated by radiofrequency energy via electrodes in contact (inserted or on the surface) with the cartilage. The cartilage is heated until the stress relaxation temperature is reached in the tissue or stress relaxation is determined through other measurement techniques including optical monitoring and acoustic monitoring. Further aspects of the invention include electrodes shaped to the final desired cartilage shape, and wherein the electrodes are integrated with clamps, jigs or scissors to perform the additional roles of holding and deforming both cartilage grafts and cartilage tissue in situ (e.g. tracheal rings in the airway). In other embodiments of the present invention, an array of electrodes are used to heat the cartilage, wherein the array electrodes may be activated either sequentially or in parallel depending upon the desired thermal field. Monitoring of the stress relaxation temperature may occur by various means, including direct measurement of the temperature, measurement of the changes in the light scattering properties of the cartilage as stress relaxation occurs, and measurement of changes in cartilage physical properties (density, electrical resistance and acoustic properties).

BRIEF DESCRIPTION OF THE DRAWINGS

FIGS. 1A and 1B illustrate aspects of the present invention utilizing electrodes that are inserted and placed on the cartilage respectively.

FIGS. 2A and 2B illustrate aspects of the present invention wherein the electrodes may be simple (e.g. arcs) or complex shapes.

FIGS. 3A and 3B illustrate aspects of the present invention wherein surface mounted electrodes provide additional functions of holding and deforming as part of a clamp, jig or scissors.

FIGS. 4A and 4B illustrate further aspects of the present invention wherein the electrodes may comprise an array of electrodes either embedded or on the surface of the RF heating element.

DETAILED DESCRIPTION OF THE INVENTION

Figure 5:
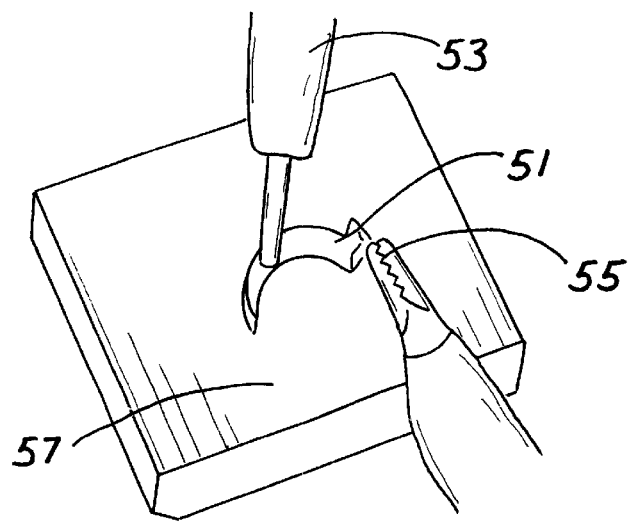
FIG. 5 illustrates an exemplary configuration of the present invention with a cartilage bending jig, cartilage specimen, grounding electrode, and RF electrode.

| Abbreviations | |
|---|---|
| ADC | analog to digital converter |
| IR | infrared |
| mm | millimeter |
| nm | nanometer |
| pc | personal computer |
| RF | radiofrequency |
| Si | silicon |

As described herein for various embodiments of the present invention, various types of RF devices may be used to heat and reshape cartilage.

Advantages of RF Generated Stress Relaxation/Reshaping

To achieve stress relaxation, it is preferred that the cartilage be heated to a temperature in the range of 60 to 75 degrees C., most preferably 70 degrees C., however the precise temperature range is dependent on the heating rate. Distinct advantages exist in using RF generated heating for thermally accelerated stress relaxation of cartilage. The technology is inexpensive and already available in most operating rooms. It requires no additional protective equipment for the operator, in contrast to laser procedures which require eye protection for the surgeon, operating room personnel, and the patient. Because contact heating is used, electrodes may be designed which also function as molds, presses, clamps, or mandrills to deform the cartilage graft or restore/alter the shape of native tissue in situ. Anatomic specimens could then be straightened (as in the case of deformed nasal septal cartilage,) or reshaped into curves of predetermined radii (for applications such as reconstruction of the trachea or nasal ala.) The ability to produce cartilage of a precise shape will minimize the invasiveness of the surgical approach, thereby reducing the morbidity for the patient.

RF Heating of Cartilage

Conduction of electrical currents within the tissue will depend on the dielectric properties of the tissue as well as the frequency, waveform and amplitude of the source and electrode design. Transmission (or application) of RF energy in biological tissue results in generation of heat due to the vibration of water molecules. The spatial distribution of heat is dependent upon the space-dependent electric field intensity and the thermal diffusivity of the cartilage specimen. The temporal characteristics of any RF generated heat source in tissue depends also upon the duration of RF heating. Lower frequencies (on the order of ½ MHz) in general result in a more volumetric, bulk heating effect due to a larger more uniform electric field. Higher frequencies (on the order of several MHz) confine the electromagnetic energy to a smaller region of space. The requirements for the specific surgical procedure (bulk heating of the entire tissue sample, or localized spot heating) will dictate the power spectrum of frequencies applied to the RF generator.

Radiofrequency (RF) Generators

In general, bipolar RF heating is preferred, but there may be some applications (such as inside the trachea) where this geometry would not be accommodated, in which case monopolar RF heating may be used.

RF Energy Modulation

RF energy input (frequency, voltage, current, power, time duration and waveform) to the cartilage affects the temperature profile in the cartilage. Since denaturation of proteoglycans and collagen takes more time than that required for stress relaxation, the time dependent nature of the temperature profile in the cartilage needs to be considered. If the energy is deposited largely at the cartilage surface and interior heating occurs primarily by heat conduction, then modulation of the energy input with time is preferred in order to prevent overheating of the surface prior to stress relaxation occurring in the interior of the cartilage. One means of accomplishing this is modification of the waveform (e.g., cycling the RF energy input on and off, altering frequency etc.). The frequencies may be selected dynamically according to the feedback control signal(s). This can provide real-time variation of the depth distribution of thermal energy deposition. In laser procedures, energy fluence on the order of 25–40 W/cm$^2$ raises tissue temperatures in 1–3 mm thick cartilage specifimens to 60–70 deg. C in 2–4 seconds. If significant energy is deposited largely at the surface, various cooling means as are well known in the art may be preferred including cooling of the electrodes or handpiece.

RF Electrodes and Reshaping Clamps/Jigs

The RF electrodes may vary in size and shape, as required for the desired reshaping, and appropriate for the cartilage size and shape, and may be monopolar or bipolar. The RF electrodes are placed in contact with the cartilage either on the surface or inserted into the tissue. Electrodes to be inserted may be of various shapes, preferably needle or knife-blade shaped. Preferred electrode material is stainless steel (medical grade) though other materials including shape memory alloys may also be useful. FIG. 1A shows needle shaped electrodes 13 that are inserted into cartilage 11 which is held by a jig (not shown). Referring to FIG. 1B, RF electrode 13 contacts the surface of unshaped cartilage 15a (e.g. nasal tip) to provide RF heating resulting in reshaped cartilage 15b. Surface contact electrodes 23, may be simple shapes, such as in a spatula or arc shape FIG. 2A, or complex shapes (FIG. 2B).

Standard medical jigs, clamps and scissors for reshaping cartilage are well known in the art. A further embodiment of the present invention is where the electrodes themselves are part of the jig, clamps or scissors, not only heating, but also serving to clamp and/or shape the tissue. The electrodes may also be designed to function as molds, presses and mandrills. Referring to FIG. 3A, unshaped cartilage 31a is heated, clamped and deformed by surface contact RF electrodes 33 resulting in reshaped cartilage 31b. The electrodes are preferably incorporated as part of a jig, clamp or scissors 35 (FIG. 3B). The electrodes may themselves be shaped into the desired shape, or coupled with (embedded into, or placed on the surface) a non-conductive, biocompatible material such as plastic. It is also possible to construct these type of electrodes from malleable materials in order to provide the use with more shape change options.

In the present invention, the electrodes may be placed and repositioned to different places on the cartilage as required for the desired temperature profile in the tissue. In a further embodiment the electrodes may be an array of electrodes, that are either simultaneously or sequentially activated. Referring to FIG. 4A, metal expandable stent 45 is placed inside the cartilage specimen 41 (e.g. tracheal ring), wherein array of electrodes 43 are positioned on the surface of stent 45. It is to be equally understood that electrode array 43 may be embedded in stent 45, which may be constructed from using plastic, metal and shape memory alloys. Stents may be of the shape memory type (inserted then heated to expand), or inflatable (balloon-bladder) type. The incorporation of RF technology into current available stents is also feasible.

Saline Solution

Use of a saline or similar electrolyte solution between the RF electrode(s) and the cartilage may be used to improve contact between the element and the tissue. The solution may also serve to provide cooling to the tissue, mitigating potential situations wherein a vapor bubble develops between the electrode(s) and tissue in dry environments. Active irrigation may improve this process by allowing for modulation of surface temperatures.

Rehydration

The cartilage may be held in position during the reshaping process, in-vitro or in-vivo. If the cartilage is heated in-vitro outside of a saline solution, the cartilage is preferably rehydrated following such heating, but while mechanically deformed. A rehydration time of approximately 15 minutes has been found to be suitable for maintenance of the new shape following laser heating, and should be equally suitable following RF heating. In-vivo, the re-shaped cartilage is often surrounded by hydrated soft cartilage and hence is an aqueous environment obviating the need for application of external solutions for rehydration, but the need for maintaining deformation will likely still be necessary (15 minutes).

Monitoring of Cartilage Stress Relaxation

As mentioned previously, stress relaxation occurs within a discrete temperature range, and therefore it is preferred that there be a means to detect the onset of stress relaxation in order to provide feedback control over the temporal and spatial characteristics of the RF heating and hence minimize thermal injury to the chondrocytes. If the RF source is manually operated, the feedback control means could serve to provide visual and/or auditory cues to the operator. If the RF source is automatically controlled, such as by a computer, the feedback control means could be linked directly to the RF source.

Temperature Measurements

Onset of stress relaxation may be detected by directly measuring temperature, either by contact methods or radiometric. If contact methods are used, it is preferred that a RF generator device with integrated micro-thermocouples be used, to monitor tissue temperature during heating.

Measurement of Changes in Cartilage Optical Properties

It has been found that thermally mediated stress relaxation in cartilage is also accompanied by changes in light scattering properties in the cartilage. Thus, observed changes in the intensity of diffusely transmitted light during RF generated heating can be used to provide feedback control over the RF power delivery. It is preferred that the wavelength of the illuminating light be in the visible to near IR range. Optical fibers can be used to deliver light to the tissue and also be used to detect backscattered light. Fibers can be incorporated into electrode, jig, clamp etc. design, and one fiber may be use to deliver light and collect the reflected or transmitted optical signal. A variety of signal processing techniques can be used to improve signal quality. Multi-wavelength probing of the tissue may also be of value, providing different qualitative changes in the reflected light curve.

Measurement of Cartilage Physical Properties

It is known that biological tissue undergoes changes in density and electrical resistance as the tissue is heated. Monitoring of changes in cartilage density or electrical resistance by means well known in the art, during RF heating may also be used to provide feedback control over the RF heating. Other easily measured physical characteristic include tissue acoustic properties which can be detected and evaluated using a variety of acoustic techniques, in general based on piezo-electric technology. This art is well known and commonly used for non-destructive testing applications.

EXAMPLES

Cartilage Preparation

For the following examples, porcine nasal septal cartilage from freshly euthanized animals was obtained from a local abattoir. (Lizzy's Custom Processing, Chino, Calif.) The specimens were cut into 20 mm×10 mm sections and then cut to a uniform thickness (2 mm) using a custom guillotine microtome. These were stored in normal saline solution at 4° C. and used within 24 hours.

Example 1

In this example, the Stortz RF generator (Stortz Surgitron #S 2100, 2.8 MHz. Elmed Inc, Addison, Ill.) used was designed primarily for tissue fulguration, coagulation and cauterization, and had an adjustable power control (uncalibrated scale from 1 to 10.) It was thus necessary to estimate the tissue effect at each power setting. This was accomplished by observing the denaturation of albumin (egg white.).

To determine approximate power settings on the Stortz RF generator for our application, albumin from fresh egg whites was used as a gross surrogate for protein coagulation and cartilage matrix denaturation. Albumin denatures at 61° C. and provides a clear visual end point for monitoring. The generator was used in bipolar mode and copper tape electrodes (6 mm×6 mm) separated by 2 mm (the thickness of the cartilage slabs) were immersed in the egg whites. Working in a well lighted room, the time required to denature the albumin (clear to white transition) was recorded across the range of power settings on the device yielding denaturation in the range of 3 to 30 seconds.

Albumin Coagulation/Denaturation

Table 1. is a tabulation of the albumin denaturation data. This allowed selection of approximate power settings of the RF generator for cartilage bending (without denaturation) and diffuse transmittance experiments. Note that the data are for 2 mm electrode separation.

TABLE 1

Time to denature egg white albumin at various power settings of the Stortz RF generator (bipolar electrodes separated by 2 mm.)

| power setting | 1.5 | 2.0 | 2.5 | 3.0 | 3.5 |
|---|---|---|---|---|---|
| time (s) | 30 | 14 | 12 | 6 | 3 |
|  | 30 | 13 | 6 | 6 | 3 |
|  |  | 17 | 6 | 6 |  |
|  |  | 11 |  |  |  |
|  |  | 16 |  |  |  |
| average time | 30 | 14 | 8 | 6 | 3 |

This process provided approximate power settings and times for the Stortz RF generator so that the proteins of the cartilage matrix could be heated without undergoing denaturation.

Reshaping (Bending) Jig

The cartilage slab 51 was placed in a wooden bending jig 57 (see FIG. 5). A grounding electrode 55 of sheet aluminum with applied conducting gel (produced for application of electrocardiogram electrodes) was placed in contact with the cartilage 51 in the jig 57. Multiple stab insertions of a needlepoint electrode 53 were made, and the device was turned on for 8 seconds at a power setting of 2 on the power scale, for each insertion. The deformed specimen was then rehydrated in normal saline for 15 minutes.

Figure 6:
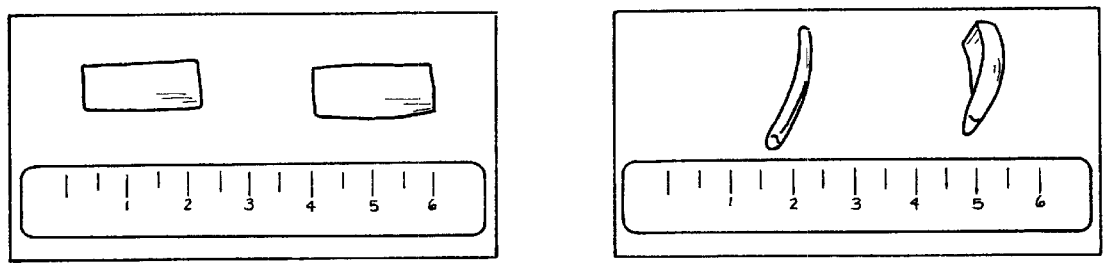
FIG. 6 provides photographs of exemplary cartilage before and after shaping by RF heating

FIG. 6 shows photographs of the cartilage specimen before and after reshaping via RF generated heating with the Stortz RF generator.

Example 2

In this example, the Somnus RF generator used (a Somnus™ model #215 Radiofrequency Generator, 460 kHz. Somnus Medical Technologies, Inc, Sunnyvale, Calif.) was originally designed for use in palatal, tongue-base and turbinate surgical procedures, and incorporates an internal microprocessor that controls heating to a user-specified temperature. The needle shaped electrode contained a series of integrated micro-thermocouples which were used to monitor the temperature of the surrounding tissue.

The cartilage was manually deformed into a curved shape with a standard surgical grounding pad applied. Multiple stab insertions of the electrode were made over the length of the cartilage slabs. At each position, the cartilage was heated to 70° C. The deformed cartilage specimens were then rehydrated in normal saline for 15 minutes. The specimens were photographed before and after reshaping.

Example 3

Figure 7:
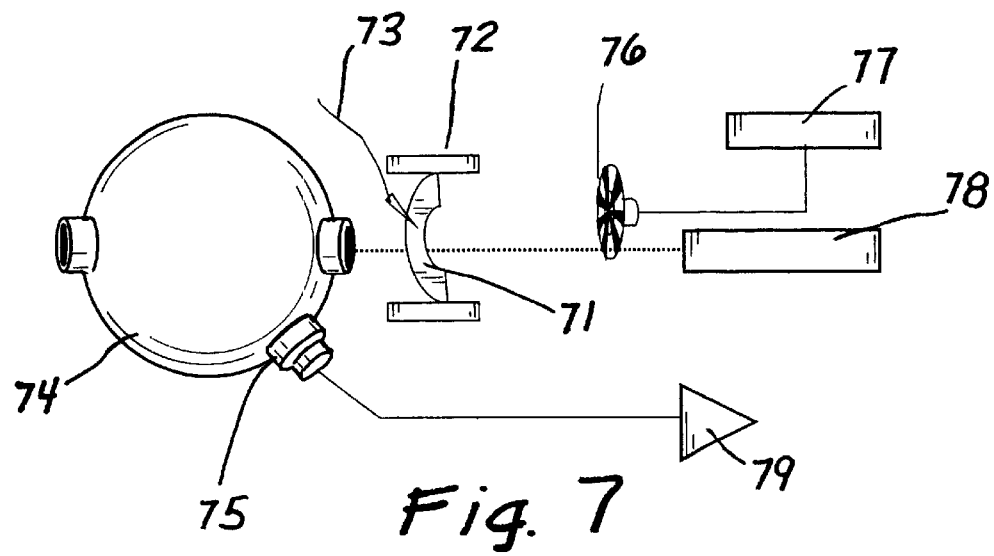
FIG. 7 illustrates an exemplary configuration of the present invention which includes light scatter measurement to provide a feedback mechanism.

In this example, laser light scattered from the specimen may be measured to monitor the degree of RF cartilage heating and stress relaxation during RF heating. Referring to FIG. 7, a diode laser 78 ($\lambda$=650 nm, 5 mW) (MWK Industries, Corona, Calif.) is directed co-linear to the surface normal of the cartilage 71 heated by needle RF electrode 73; cartilage 71 being held in jig 72. A mechanical chopper 76 and controller 78 (SR540, Stanford Research Systems, Sunnyvale, Calif.) is used to modulate the intensity of the diode laser. The intensity of the diffusely transmitted laser light I is measured using an integrating sphere 74 (LPM-040-IG, Labsphere, North Sutton, N.H.) positioned on the opposite side of the cartilage from the incident laser light. The signal is synchronously detected using a silicon photo-receiver 75 (Model 2001; New Focus, Mountain View, Calif.) and a lock-in amplifier 79 (time, 300 ms)(Model SR 850 DSP; Stanford Research Systems.) Data is acquired using a 16-bit AD converter (not shown) (AT-MIO-16XE-50; National Instruments, Austin, Tex.) and a personal computer (not shown) running software written in LabView (National Instruments.). I(t) is recorded during RF heating with the Stortz generator at a power setting of 1.25 over 30 seconds.

Figure 8:
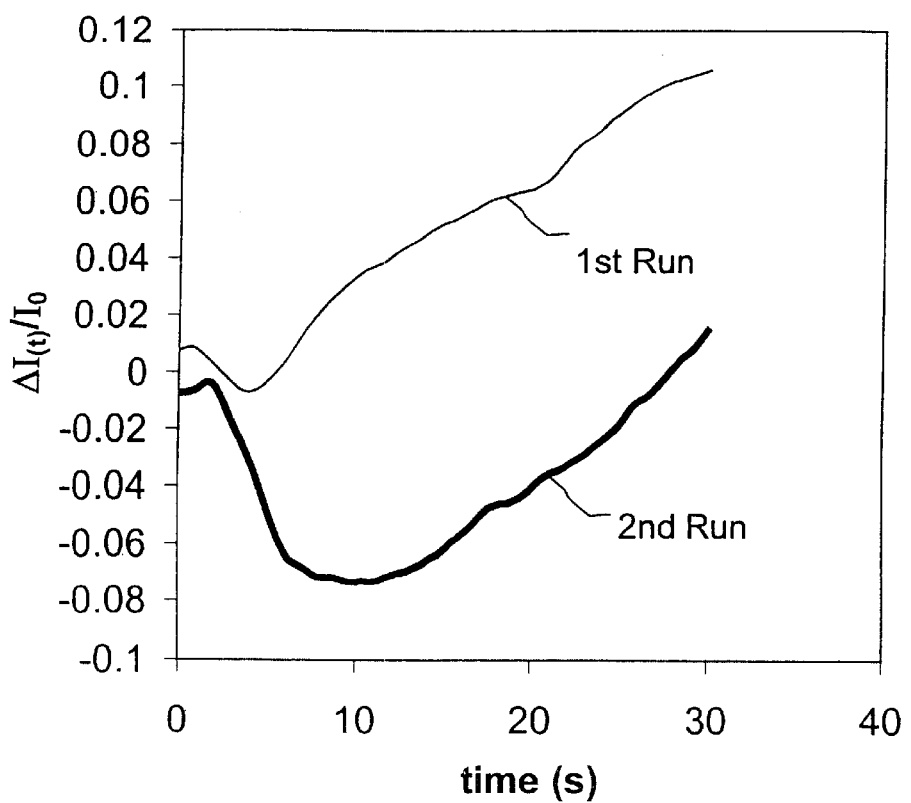
FIG. 8 illustrates diffuse transmittance vs. time for a exemplary cartilage specimen undergoing two cycles of RF heating.

Exemplary diffuse transmittance I(t) during RF generated heating is depicted in FIG. 8. Two heating cycles in the same specimen are represented. A five-minute cooling interval elapsed between cycles. It is noted that the slope of the $\Delta I(t)/I_0$ vs. time plot reaches zero at approximately 4 s with the $1^{st}$ heating and at approximately 10 s with the $2^{nd}$ heating (I(t)=intensity at time t; $I_0$=initial intensity).

The correlation between tissue optical properties and accelerated stress relaxation in mechanically deformed cartilage during laser heating has previously been documented. In particular, the slope of I(t) been shown to be zero at the onset of stress relaxation. In this study, the intensity of diffusely transmitted light through the tissue was measured during RF heating. As expected, a gradual decrease in the intensity of the transmitted laser light was observed as the tissue was heated, and the slope of the I(t) was zero after 4 to 10 s. This is within the time interval demonstrated to maintain tissue viability in previous studies.

As can be seen, thermally accelerated stress relaxation of cartilage is achievable with RF generated heating. Obviously, numerous modifications and variations of the present invention are possible in the light of the above teachings. It is therefore to be understood that within the scope of the appended claims the invention may be practiced otherwise than as specifically described therein.

What is claimed is:

1. An apparatus to reshape cartilage comprising:
   means for holding and deforming said cartilage to a desired final shape;
   means for imparting RE energy to said cartilage in order to raise its temperature wherein stress relaxation occurs;
   means for determining when said cartilage has reached the stress relaxation point; and
   means to provide a feedback signal to said RE energy means to cease or reduce the RE energy input to said cartilage when the stress relaxation point has been reached.

2. The apparatus as recited in claim 1 wherein:
   said stress relaxation determining means comprises means to monitor the temperature of said cartilage.

3. The apparatus as recited in claim 1 wherein:

said stress relaxation determining means comprises means to monitor cartilage physical properties selected from the group consisting of density, electrical resistance, and tissue acoustic properties.

4. The apparatus as recited in claim 1 wherein:

said stress relaxation determining means comprises means to measure changes in light scattering properties in said cartilage.

5. The apparatus as recited in claim 4 wherein said light scatter measurement means comprises:

a laser having wavelength selected from the visible to IR range and adapted to illuminate said cartilage; and a means to detect and collect illuminating light scattered from said cartilage.

6. The apparatus as recited in claim 1 wherein:

the means for imparting RF energy, the means for determining, and the means to provide a feedback signal are adapted to heat said cartilage to a temperature in the range of 60 to 75 degrees C.

7. The apparatus as recited in claim 6 wherein:

the means for imparting RF energy, the means for determining, and the means to provide a feedback signal are adapted to heat said cartilage to a temperature of 70 degrees C.

8. The apparatus as recited in claim 1 wherein:

said RF energy means comprises one or more electrodes connected to an RF generator selected from the group consisting of bipolar and monopolar RF generators, with said electrode adapted to be in contact with said cartilage.

9. The apparatus as recited in claim 8 wherein:

said electrode adapted to make contact with said cartilage by insertion of said electrode.

10. The apparatus as recited in claim 9 wherein:

said electrode is needle or knife-blade shaped.

11. The apparatus as recited in claim 8 wherein:

said electrode is adapted to contact the surface of said cartilage.

12. The apparatus as recited in claim 11 wherein:

said electrode is shaped to provide the final desired shape.

13. The apparatus as recited in claim 11 wherein:

said electrode has a spatula or arc shape.

14. The apparatus as recited in claim 11 wherein:

said holding-deforming means is selected from the group consisting of jigs, molds, presses, mandrills, clamps and scissors that integrates said electrode and is adapted to also deform said cartilage.

15. The apparatus as recited in claim 14 wherein;

said electrode is made from a shape memory alloy.

16. The apparatus as recited in claim 8 wherein:

said electrodes comprise an array of electrodes adapted to be in contact with said cartilage.

17. The apparatus as recited in claim 16 wherein:

said electrodes are activated either sequentially or in parallel.

18. The apparatus as recited in claim 1 wherein:

the frequency of said RF energy is selected from the range of on the order of ½ MHz to on the order of several MHz.

19. The apparatus as recited in claim 18 wherein:

the frequency is selected dynamically according to the feedback control signal(s).

20. The apparatus as recited in claim 8 wherein:

said electrodes are embedded in a non-conductive biocompatible material.

21. A method to reshape cartilage comprising the steps of:

holding and deforming said cartilage to a desired final shape;

imparting RE energy to said cartilage in order to raise its temperature wherein stress relaxation occurs;

determining when said cartilage has reached the stress relaxation point; and providing a feedback signal to said RE energy means to cease or reduce the RF energy input to said cartilage when the stress relaxation point has been reached.

22. The method as recited in claim 21 wherein:

said stress relaxation determining step comprises monitoring the temperature of said cartilage.

23. The method as recited in claim 21 wherein:

said stress relaxation determining step comprises monitoring cartilage physical properties selected from the group consisting of density, electrical resistance, and tissue acoustic properties.

24. The method as recited in claim 21 wherein:

said stress relaxation determining step comprises measuring changes in light scattering properties in said cartilage.

25. The method as recited in claim 24 wherein:

said step of measuring changes in light scattering properties comprises illuminating said cartilage with a laser having wavelength selected from the visible to IR range, and detecting and collecting the illuminating light scattered from said cartilage.

26. The method as recited in claim 21 wherein:

said steps of imparting, determining, and providing achieve a step of heating said cartilage to a temperature in the range of 60 to 75 degrees C.

27. The method as recited in claim 26 wherein:

said steps of imparting, determining, and providing achieve a step of heating said cartilage to a temperature of 70 degrees C.

28. The method as recited in claim 21 wherein said RF energy imparting step further comprises:

utilizing one or more electrodes connected to an RF generator selected from the group consisting of bipolar and monopolar RF generators; and contacting said cartilage with said electrode.

29. The method as recited in claim 28 wherein said step of contacting further comprises inserting said electrode.

30. The method as recited in claim 29 wherein said step of imparting and utilizing further comprise:

providing said electrode in a shape of a needle or a knife-blade.

31. The method as recited in claim 28 wherein said step of contacting further comprises:

placing said electrode in contact with the surface of said cartilage.

32. The method as recited in claim 31 further comprising:

providing said electrode in the desired shape.

33. The method as recited in claim 31 further comprising:

providing said electrode in a spatula or arc shape.

34. The method as recited in claim 31 wherein said holding and deforming step further comprises:

utilizing an implement selected from the group consisting of jigs, molds, presses, mandrills, clamps and scissors; and integrating said electrode to deform said cartilage.

35. The apparatus as recited in claim 34 further comprising;

providing said electrode made from a shape memory alloy.

36. The apparatus as recited in claim 28 wherein:

said step of utilizing comprises utilizing an array of electrodes; and said step of contacting comprises contacting said cartilage with said array of electrodes.

37. The apparatus as recited in claim 36 further comprising:

activating said electrodes either sequentially or in parallel.

38. The method as recited in claim 21 further comprising:

selecting the frequency of said RF energy from the range of on the order of ½ MHz to on the order of several MHz.

39. The method as recited in claim 38 further comprising:

selecting the frequency dynamically according to the feedback control signal(s).

* * * * *

UNITED STATES PATENT AND TRADEMARK OFFICE
CERTIFICATE OF CORRECTION

| | |
|---|---|
| PATENT NO. | : 6,589,235 B2 |
| APPLICATION NO. | : 09/770799 |
| DATED | : July 8, 2003 |
| INVENTOR(S) | : Brian J. F. Wong et al. |

It is certified that error appears in the above-identified patent and that said Letters Patent is hereby corrected as shown below:

Replace the text of column 1, lines 15-20 with the following language:

-- This invention was made with government support under Grant No. 95-3800459 awarded by the Department of Energy, Grant No. N00014-94-0874 awarded by the Office of Naval Research, and Grant Nos. 1 K08 DC 00170-01, AR-43419, RR-01192, and HL-59472 awarded by the National Institutes of Health. The government has certain rights in the invention.--

Signed and Sealed this

Twenty-third Day of February, 2010

David J. Kappos
*Director of the United States Patent and Trademark Office*